(12) United States Patent
Kozawa

(10) Patent No.: US 11,187,685 B2
(45) Date of Patent: Nov. 30, 2021

(54) NOISE LEVEL ESTIMATION METHOD, MEASUREMENT DATA PROCESSING DEVICE, AND PROGRAM FOR PROCESSING MEASUREMENT DATA

(71) Applicant: SHIMADZU CORPORATION, Kyoto (JP)

(72) Inventor: Hiroaki Kozawa, Omihachiman (JP)

(73) Assignee: SHIMADZU CORPORATION, Kyoto (JP)

( * ) Notice: Subject to any disclaimer, the term of this patent is extended or adjusted under 35 U.S.C. 154(b) by 451 days.

(21) Appl. No.: 15/549,432

(22) PCT Filed: Feb. 16, 2015

(86) PCT No.: PCT/JP2015/054068
§ 371 (c)(1),
(2) Date: Aug. 8, 2017

(87) PCT Pub. No.: WO2016/132422
PCT Pub. Date: Aug. 25, 2016

(65) Prior Publication Data
US 2018/0003683 A1    Jan. 4, 2018

(51) Int. Cl.
*G01N 30/86*     (2006.01)
*G01N 30/62*     (2006.01)
(Continued)

(52) U.S. Cl.
CPC ......... *G01N 30/8675* (2013.01); *G01N 30/86* (2013.01); *G01N 30/8617* (2013.01);
(Continued)

(58) Field of Classification Search
None
See application file for complete search history.

(56) References Cited

U.S. PATENT DOCUMENTS

| 4,837,726 A | * | 6/1989 | Hunkapiller | ....... G01N 30/8641 |
|  |  |  |  | 702/32 |
| 5,966,684 A | * | 10/1999 | Richardson | ............ H04B 1/123 |
|  |  |  |  | 702/190 |

(Continued)

FOREIGN PATENT DOCUMENTS

| EP | 0 296 781 A2 | 12/1988 |  |
| EP | 0296781 A2 * | 12/1988 | ......... G01N 30/8641 |

(Continued)

OTHER PUBLICATIONS

Liland et al; "Optimal Choice of Baseline Correction for Multivariate Calibration of Spectra"; Applied Spectroscopy, vol. 64, No. 9, 2010. (Year: 2010).*

(Continued)

*Primary Examiner* — Catherine T. Rastovski
*Assistant Examiner* — Leonard S Liang
(74) *Attorney, Agent, or Firm* — Sughrue Mion, PLLC

(57) ABSTRACT

A method includes: performing a time-frequency analysis on measurement data to obtain waveform data representing a temporal change in the intensity of each of a plurality of frequency components; dividing the waveform data of each of a plurality of predetermined frequencies into a plurality of segments so that each section where positive values successively occur and each section where negative values successively occur in a time-axis direction are defined as one segment; calculating the area of each of the segments to obtain segment values; creating, for the waveform data of each of the predetermined frequency components, a selected segment group by excluding a segment whose segment value exceeds a predetermined reference value from the segments in the waveform data; and determining a noise level of each of the predetermined frequency components (Continued)

based on the average value of the segment values of the segments included in the selected segment group.

10 Claims, 5 Drawing Sheets

(51) Int. Cl.
*G01N 30/88* (2006.01)
*G01N 33/00* (2006.01)
*H01J 49/00* (2006.01)

(52) U.S. Cl.
CPC ..... *G01N 30/8624* (2013.01); *G01N 30/8631* (2013.01); *G01N 30/62* (2013.01); *G01N 30/861* (2013.01); *G01N 30/8641* (2013.01); *G01N 30/88* (2013.01); *G01N 33/00* (2013.01); *H01J 49/0036* (2013.01)

(56) References Cited

U.S. PATENT DOCUMENTS

| | | | | |
|---|---|---|---|---|
| 6,112,161 A * | 8/2000 | Dryden | ............ | G01N 30/8603 702/111 |
| 6,449,584 B1 * | 9/2002 | Bertrand | ................ | G06F 17/10 702/180 |
| 7,340,375 B1 | 3/2008 | Patenaud et al. | | |
| 7,409,298 B2 * | 8/2008 | Andreev | ............ | G01N 30/8603 702/23 |
| 7,657,387 B2 * | 2/2010 | Malek | .................... | H03M 7/30 702/66 |
| 7,983,852 B2 * | 7/2011 | Wright | .............. | G01N 30/8624 702/32 |
| 8,027,743 B1 * | 9/2011 | Johnston | ............ | G10L 21/0208 700/94 |
| 8,530,828 B2 * | 9/2013 | Ivosev | ................ | H01J 49/0036 250/281 |
| 9,177,559 B2 * | 11/2015 | Stephenson | ............ | G10L 17/26 |
| 10,359,404 B2 * | 7/2019 | Kozawa | ............... | G01N 30/861 |
| 2003/0009091 A1 * | 1/2003 | Edgar, Jr. | ............. | A61B 5/7207 600/323 |
| 2005/0261838 A1 * | 11/2005 | Andreev | ............ | G01N 30/8603 702/22 |
| 2005/0285023 A1 | 12/2005 | Liu | | |
| 2006/0241491 A1 * | 10/2006 | Bosch-Charpenay | .... | G01J 3/45 600/473 |
| 2006/0241937 A1 * | 10/2006 | Ma | .......................... | G10L 25/78 704/206 |
| 2007/0143319 A1 * | 6/2007 | Malek | ................ | H01J 49/0036 |
| 2008/0270083 A1 * | 10/2008 | Lange | ................ | G06K 9/00523 702/193 |
| 2009/0199620 A1 * | 8/2009 | Kawana | ............ | G01N 30/8603 73/23.37 |
| 2010/0030562 A1 * | 2/2010 | Yoshizawa | .......... | G10L 21/0208 704/270 |
| 2010/0208902 A1 * | 8/2010 | Yoshizawa | .......... | G10L 21/0208 381/56 |
| 2010/0215191 A1 * | 8/2010 | Yoshizawa | .......... | G10L 21/0208 381/94.2 |
| 2010/0283785 A1 * | 11/2010 | Satulovsky | .......... | G01N 27/447 345/440 |
| 2011/0054804 A1 * | 3/2011 | Pfaff | ...................... | G01N 30/72 702/25 |
| 2012/0089344 A1 * | 4/2012 | Wright | .................... | G01J 3/28 702/32 |
| 2013/0087701 A1 * | 4/2013 | Ivosev | ................... | H01J 49/26 250/282 |
| 2013/0131998 A1 * | 5/2013 | Wright | .............. | G01N 30/8675 702/27 |
| 2013/0311110 A1 * | 11/2013 | Aizikov | .............. | H01J 49/0036 702/32 |
| 2014/0079248 A1 * | 3/2014 | Short | .................. | G10L 21/0272 381/119 |
| 2014/0142894 A1 * | 5/2014 | Chang | .................... | G06F 17/18 702/181 |
| 2014/0177868 A1 * | 6/2014 | Jensen | .................. | H04R 3/002 381/94.7 |
| 2014/0180682 A1 * | 6/2014 | Shi | ...................... | G10L 21/0216 704/207 |
| 2014/0252218 A1 * | 9/2014 | Wright | ............... | H01J 49/0036 250/282 |
| 2015/0287422 A1 * | 10/2015 | Short | .................... | G01S 13/723 704/205 |
| 2016/0224830 A1 * | 8/2016 | Noda | ................. | G01N 30/8634 |
| 2017/0336370 A1 * | 11/2017 | Noda | .................... | G01N 30/86 |
| 2018/0011067 A1 * | 1/2018 | Kozawa | ............. | G01N 30/8641 |

FOREIGN PATENT DOCUMENTS

| | | | | |
|---|---|---|---|---|
| JP | 62291562 A | * | 12/1987 | |
| JP | 07-098270 A | | 4/1995 | |
| JP | 11153588 A | * | 6/1999 | ......... G01N 30/8603 |
| JP | 2006-163614 A | | 6/2006 | |
| JP | 2009008582 A | * | 1/2009 | |
| JP | 2009204397 A | * | 9/2009 | |
| JP | 2012177568 A | * | 9/2012 | |
| JP | 2014137350 A | * | 7/2014 | |
| JP | 2015200532 A | * | 11/2015 | |

OTHER PUBLICATIONS

Zhang et al; "Multiscale peak alignment for chromatographic datasets"; Journal of Chromatography A, vol. 1223, Feb. 3, 2012, pp. 93-106. (Year: 2012).*
Machine Translation for JP2009008582 (Year: 2009).*
Machine Translation for JP2009204397 (Year: 2009).*
Machine Translation for JP2012177568 (Year: 2012).*
Machine Translation for JP2014137350 (Year: 2014).*
Machine Translation for JP2015200532 (Year: 2015).*
Machine Translation for JPH11153588 (Year: 1999).*
Machine Translation for JPS62291562 (Year: 1987).*
Wikipedia Entry about normalization (i.e. Normalization Wiki) (snapshot taken on Dec. 19, 2014 using Wayback Machine; https://web.archive.org/web/20141219154944/https:en.wikipedia.org/wiki/Normalization_(statistics).) (Year: 2014).*
Li-Thiao-Te, Sebastien & Schwikowski, Benno (2012). Feature Detection with Controlled Error Rates in LC/MS Images. Journal of Computational Biology, 19(4). https:doi.org/10.1089/cmb.2009.0125 (Year: 2012).*
Payne et al., "A Signal Filtering Method for Improved Quantification and Noise Discrimination in Fourier Transform Ion Cyclotron Resonance Mass Spectrometry-Based Metabolomics Data", American Society for Mass Spectrometry, Jun. 1, 2009, vol. 20, No. 6, XP026494910, pp. 1087-1095.
Communication dated Oct. 30, 2017 from the European Patent Office in counterpart Application No. 15882527.3.
Written Opinion dated Apr. 28, 2015 in application No. PCT/JP2015/054068.
International Search Report of PCT/JP2015/054068 dated Apr. 28, 2015 English.

* cited by examiner

NOISE LEVEL ESTIMATION METHOD, MEASUREMENT DATA PROCESSING DEVICE, AND PROGRAM FOR PROCESSING MEASUREMENT DATA

CROSS REFERENCE TO RELATED APPLICATIONS

This application is a National Stage of International Application No. PCT/JP2015/054068 filed Feb. 16, 2015, the contents of which are incorporated herein by reference in its entirety.

TECHNICAL FIELD

The present invention relates to a method for estimating the magnitude of a noise component (noise level) in a chromatogram, spectrum or other kinds of measurement data, as well as a device for processing such measurement data and a program for processing measurement data.

BACKGROUND ART

One type of device for analyzing components contained in a liquid sample is the liquid chromatograph. In a liquid chromatograph, a liquid sample is carried by a stream of mobile phase and introduced into a column. The components in the sample are temporally separated within the column and subsequently detected with a detector, such as an absorptiometer, to create a chromatogram Each component is identified from the position of a peak on the chromatogram, and the concentration of that component is determined from the height or area of that peak (for example, see Patent Literature 1).

A chromatogram obtained through a measurement normally contains a noise component in addition to the peak component. The magnitude of the peak component changes with the elution of the various components contained in the liquid sample. On the other hand, the magnitude of the noise component fluctuates due to various factors. Since it is impossible to identify all of those fluctuating factors and calculate the magnitude of the noise component, the task of removing a noise component from a chromatogram to obtain a peak component has conventionally been performed by approximating the noise component by white noise and fitting it to the measurement data, or by estimating the noise component for the entire chromatogram from a portion which is considered to include no peak in the chromatogram obtained by a measurement.

CITATION LIST

Patent Literature

Patent Literature 1: JP 7-98270 A
Patent Literature 2: JP 2006-163614 A

SUMMARY OF INVENTION

Technical Problem

As noted earlier, the noise component in an actual chromatogram fluctuates due to various factors. Therefore, the approximation by white noise may be insufficient to estimate the magnitude of the noise component with high accuracy. In the case of estimating the noise component from a portion of a measured chromatogram, it is preferable to deduce the portion in the chromatogram which contains absolutely no peak component. However, this is a difficult task, and therefore, it is difficult to estimate the magnitude of the noise component with high accuracy.

Although the previous description is concerned with the case of a chromatogram, similar problems can also occur in various other kinds of measurement data which contain a peak component and noise component, such as an optical spectrum in spectrophotometry or a mass spectrum in mass spectrometry.

The problem to be solved by the present invention is to provide a noise level estimation method, measurement data processing device, and program for processing measurement data by which the magnitude of the noise component (noise level) contained in measurement data, such as a chromatogram or spectrum, can be estimated with high accuracy.

Solution to Problem

FIG. 1 shows one example of the waveforms (profiles) of a peak component (a), noise component (b) and their sum (c) as well as the power spectra respectively obtained by Fourier-transforming those profiles. A comparison of the power spectra in FIG. 1 demonstrates that a presence of a peak in a chromatogram causes an increase in the spectrum intensity at frequencies lower than a certain frequency. The present inventor has noticed this fact and conceived the present invention.

The first aspect of the present invention developed for solving the previously described problem is a method for estimating a magnitude of a noise component from measurement data containing a peak component and noise component obtained by measuring an intensity of a signal which changes with respect to a predetermined physical quantity, the method including:

a) performing a time-frequency analysis on the measurement data to obtain, for each of a plurality of predetermined frequencies, waveform data representing a change in the intensity of the frequency component concerned in the aforementioned signal with respect to the predetermined physical quantity;

b) dividing the waveform data of each of the plurality of predetermined frequencies into a plurality of segments so that each section where positive values successively occur and each section where negative values successively occur in the direction of the change in the physical quantity are defined as one segment, or so that each section between a local maximum and a local minimum neighboring each other in the direction of the change in the physical quantity is defined as one segment;

c) determining the magnitude of each of the plurality of segments in the waveform data of each of the plurality of predetermined frequencies;

d) creating, for the waveform data of each of the plurality of predetermined frequencies, a selected segment group by excluding a segment whose magnitude exceeds a predetermined reference value from the plurality of segments in the waveform data; and e) determining a noise level of each of the plurality of predetermined frequency components by calculating a statistical value of the magnitudes of the segments included in the selected segment group.

For example, the predetermined physical quantity is time, wavelength or mass-to-charge ratio, while the measurement data is, for example, a chromatogram, optical spectrum or mass spectrum.

The time-frequency analysis is an analytical technique used in such fields as the image processing. Specifically, the continuous wavelet transform, discrete wavelet transform, filter bank and other techniques are commonly known (for example, see Patent Literature 2). In the case of using the continuous wavelet transform, waveform data are acquired at a plurality of continuous frequencies, from which a set of waveform data to be used is extracted at each of a plurality of relevant frequencies. In the case of using the filter bank or discrete wavelet transform, a plurality of relevant frequencies are previously set, and a set of waveform data is acquired at each of those frequencies. The plurality of predetermined frequencies may be set by analysis operators each time, or a plurality of standard frequencies may be previously set.

The use of the term "time-frequency analysis" does not mean that the predetermined physical quantity is limited to time. The method according to the present invention is also applicable in an analysis of other kinds of data, such as optical spectrum data in which the predetermined physical quantity is wavelength, or mass spectrum data in which the predetermined physical quantity is mass-to-charge ratio.

The "magnitude" of a segment can be determined, for example, from the area or height of the segment. The "predetermined reference value" may be, for example, the average+Nσ of the magnitudes of the segments (where N is a positive integer, and a is the unbiased standard deviation), or the median+M×MAD (median absolute deviation) of the magnitudes of the segments (where M is a positive integer). The reference value may also be determined from the distribution of the magnitudes of the segments included in the same set of waveform data, by finding the range which includes a specific proportion (e.g. 90% of those segments and designating the upper limit of that range as the reference value. The "statistic value" of the magnitudes of the segments included in the selected segment group may be, for example, the average or median of the magnitudes of the segments forming the selected segment group.

In the noise level estimation method according to the present invention, a segment whose magnitude exceeds the predetermined reference value is regarded as a segment originating from the peak component and excluded from the plurality of segments included in the waveform data. Therefore, the noise level of the measurement data can be estimated with high accuracy.

The noise level in a chromatogram is not always at the same level. For example, in a gradient analysis, the noise level may fluctuate due to the temporal change in the mixture ratio of the solutions constituting the mobile phase. The noise level may also fluctuate due to a change in the temperature around the device during the measurement of a chromatogram. In these types of measurement data, an increase in the noise level causes the segment to be larger in magnitude, so that a segment originating from the noise component may be inappropriately excluded.

Accordingly, the noise level estimation method may preferably include:

normalizing the magnitude of each of the plurality of segments before creating the selected segment group, using index data concerning a change in the magnitude of the noise component in the direction of the change in the physical quantity in the measurement data.

For example, a set of data showing the change in the mixture ratio of the solutions in a gradient analysis, or a set of data showing the temperature change during the acquisition of the measurement data, may be used as the index data. By using, as the index data, those data which are expected to affect the rise and fall of the noise level, it is possible to more correctly create the selected segment group and estimate the noise level with a higher level of accuracy.

The noise level estimation method according to the present invention may be configured so that:

the selected segment group is created by excluding a segment which is located at a position corresponding to the aforementioned excluded segment in the direction of the change in the predetermined physical quantity and which belongs to the waveform data at a lower frequency than the frequency of the waveform data to which the aforementioned excluded segment belongs.

The power spectrum of the peak component (a) shown in FIG. 1 demonstrates that, for a peak component that is present at a certain frequency, there is certainly a peak component within the frequency range lower than that frequency. Therefore, if there is a segment located at a position in the direction of the change in the predetermined physical quantity (e.g. in the time-axis direction) corresponding to a segment which has been excluded as a segment originating from a peak, and if that segment belongs to waveform data at a lower frequency than the waveform data to which the excluded segment belongs, the segment concerned can be judged to be a segment originating from the peak. By excluding these segments, all segments originating from the peak can be excluded without omission, and the noise level can be estimated with an even higher level of accuracy.

The noise level estimation method according to the present invention may further include:

comparing the noise levels at the plurality of predetermined frequencies with each other, and correcting the noise levels so that the noise level at a lower frequency becomes equal to or higher than the noise level at a higher frequency.

In a measurement of a signal intensity which changes with respect to a predetermined physical quantity, a detector which includes an electrical circuit having a capacitor or an analogue-to-digital (A/D) converter responding with a predetermined time constant is normally used. It is commonly known that a capacitor which accumulates electric charges for a predetermined period of time, or an A/D converter which responds with a predetermined time constant, acts like a low-pass filter and decreases the signal within a high frequency range. Therefore, the noise level in a signal acquired through such a detector tends to increase from higher to lower frequencies. Accordingly, by correcting the noise level in a manner to reflect such a tendency, the noise level can be even more accurately determined.

The second aspect of the present invention developed for solving the previously described problem is a measurement data processing device used for estimating a magnitude of a noise component from measurement data containing a peak component and noise component obtained by measuring an intensity of a signal which changes with respect to a predetermined physical quantity, the device including:

a) a time-frequency analyzer for performing a time-frequency analysis on the measurement data to obtain, for each of a plurality of predetermined frequencies, waveform data representing a change in the intensity of the frequency component concerned in the aforementioned signal with respect to the predetermined physical quantity;

b) a segment divider for dividing the waveform data of each of the plurality of predetermined frequencies into a plurality of segments so that each section where positive values successively occur and each section where negative values successively occur in the direction of the change in the physical quantity are defined as one segment, or so that each section between a local maximum and a local minimum neighboring each other in the direction of the change in the physical quantity is defined as one segment;

c) a segment value calculator for determining the magnitude of each of the plurality of segments in the waveform data of each of the plurality of predetermined frequency components;

d) a selected segment group creator for creating, for the waveform data of each of the plurality of predetermined frequency components, a selected segment group by excluding a segment whose magnitude exceeds a predetermined reference value from the plurality of segments in the waveform data; and e) a noise level calculator for determining a noise level of each of the plurality of predetermined frequency components by calculating a statistical value of the magnitudes of the segments included in the selected segment group.

The third aspect of the present invention developed for solving the previously described problem is a program for processing measurement data used for estimating a magnitude of a noise component from measurement data containing a peak component and noise component obtained by measuring and intensity of a signal which changes with respect to a predetermined physical quantity, the program characterized by making a computer function as the measurement data processing device according to the second aspect of the present invention.

Advantageous Effects of the Invention

With the noise level estimation method, measurement data processing device or program for processing measurement data according to the present invention, the magnitude of a noise component (noise level) in a chromatogram, spectrum or other kinds of measurement data can be estimated with high accuracy.

DESCRIPTION OF EMBODIMENTS

Embodiments of the noise level estimation method, measurement data processing device, and program for processing measurement data according to the present invention are hereinafter described with reference to the attached drawings. The following embodiments deal with the case of estimating a noise level which is the magnitude of a noise component contained in a chromatogram acquired using a liquid chromatograph.

Figure 1:
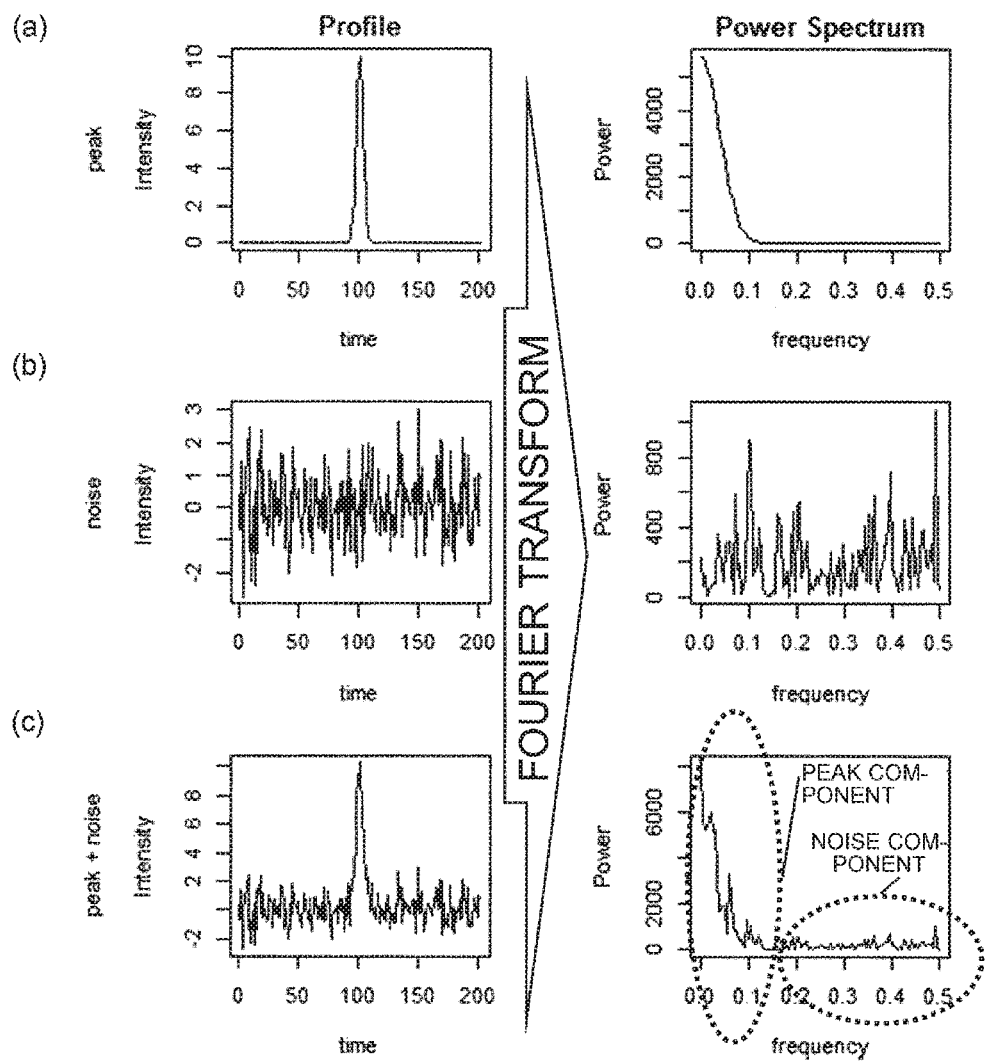
FIG. 1 shows waveforms of a peak component, noise component and their sum as well as their respective power spectra.
Figure 2:
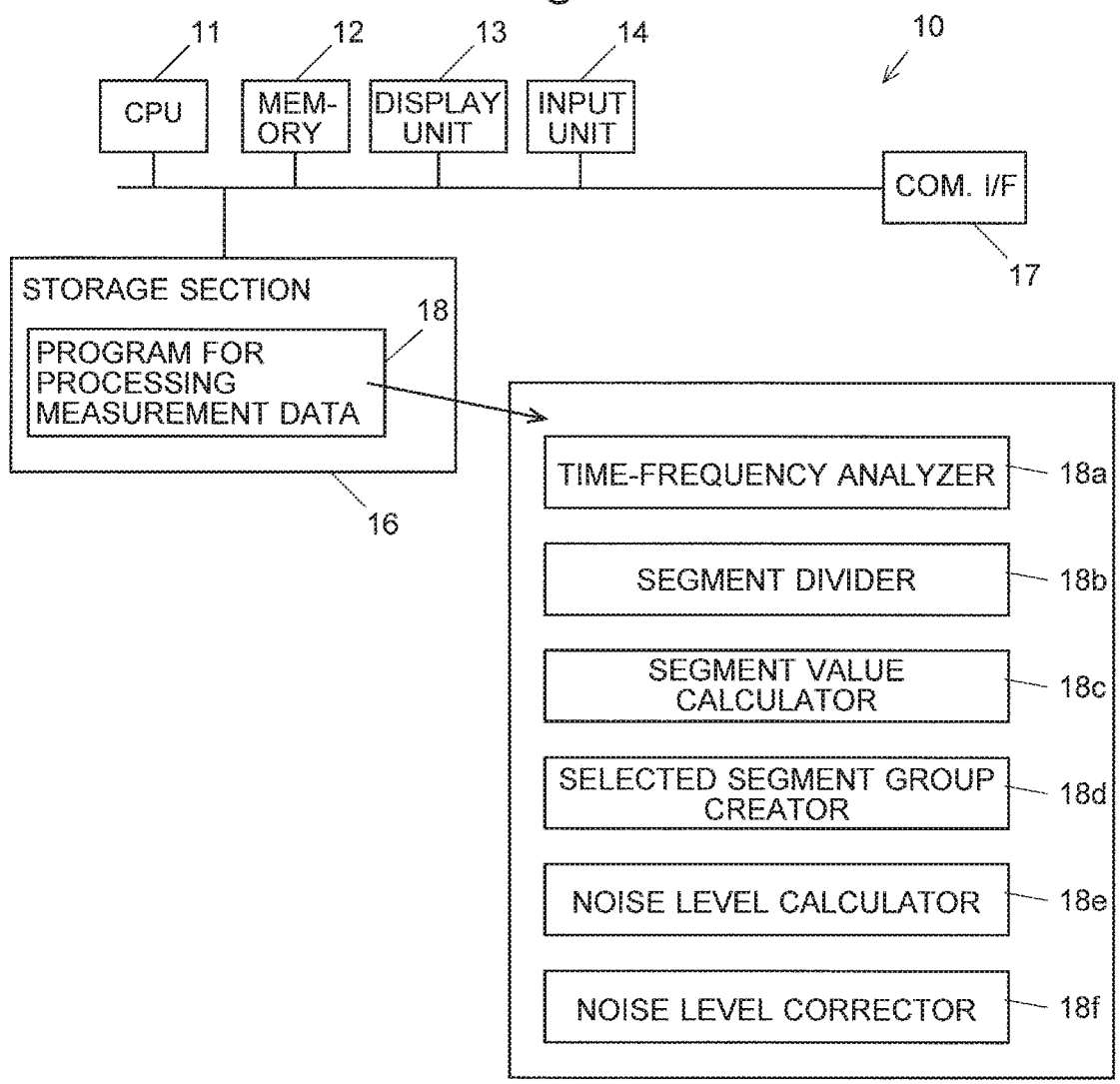
FIG. 2 is a configuration diagram of one embodiment of the measurement data processing device according to the present invention.

FIG. 2 shows the configuration of a measurement data processing device 10 according to the present embodiment. The measurement data processing device 10 is actually a general-purpose personal computer provided with a central processing unit (CPU) 11, memory 12, display unit (monitor) 13, input unit 14, storage section 16 including a high-volume storage device (e.g. hard disk), communication interlace (com. I/F) 17, and other elements. The measurement data processing device 10 can be connected to a liquid chromatograph (not shown) through the communication interface 17.

In the storage section 16, index data which has been prepared along with the acquisition of the chromatogram data is stored. For example, the index data is a set of data recording a temporal change of a parameter which affects the rise and fall of the noise level, such as the temporal change in the solution mixture ratio during a gradient analysis or the temporal change in the ambient temperature inside the measurement room. An OS (operating system) and a program 18 for processing measurement data are also stored in the storage section 16. Executing the program 18 for processing measurement data makes the CPU 11 function as a time-frequency analyzer 18a, segment divider 18b, segment value calculator 18c, selected segment group creator 18d, noise level calculator 18e and noise level corrector 18f, all of which will be described later.

Figure 3:
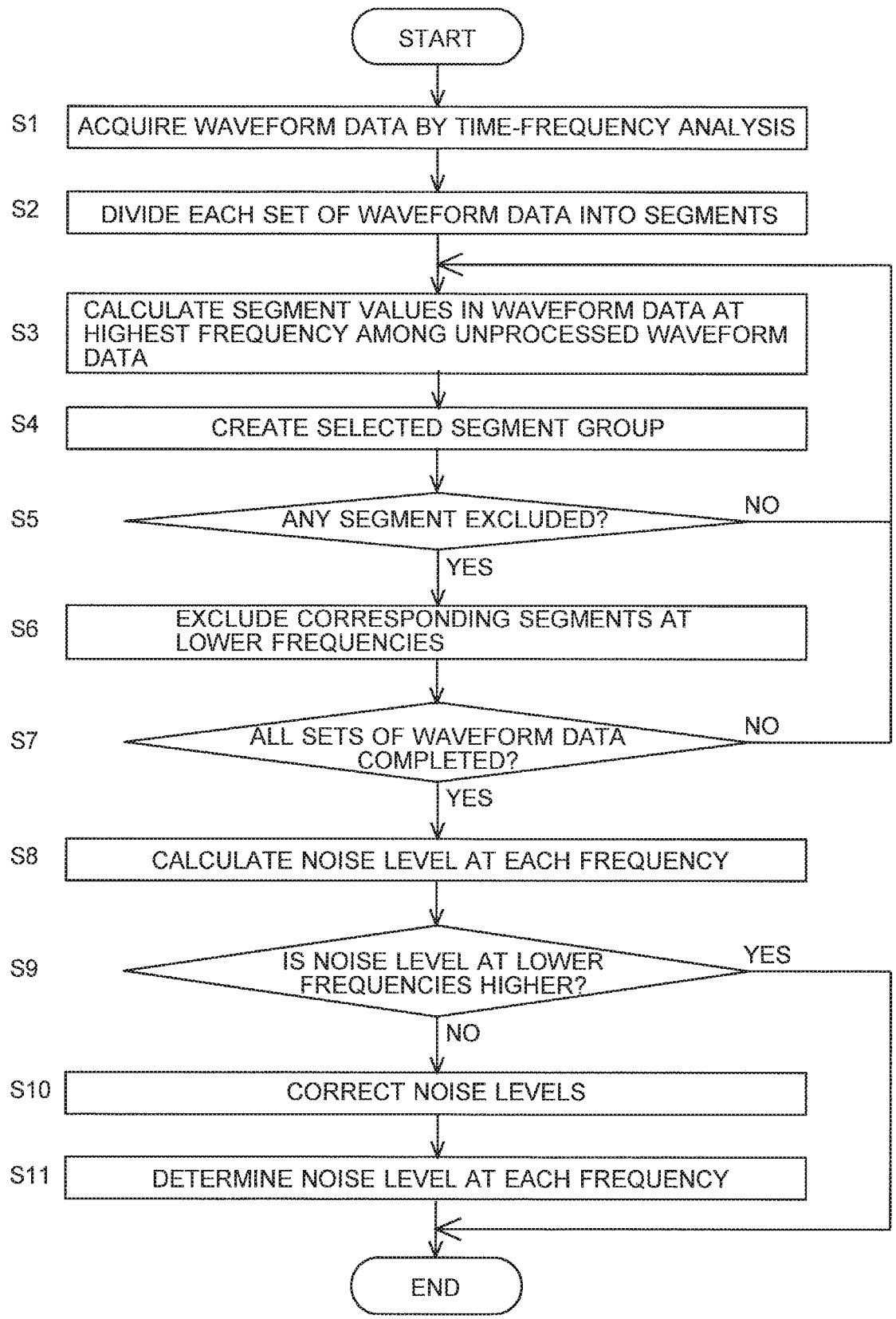
FIG. 3 is a flowchart in the noise level estimation method of the present embodiment.

The noise level estimation method using the measurement data processing device 10 of the present embodiment is hereinafter described with reference to the flowchart of FIG. 3.

Figure 4A:
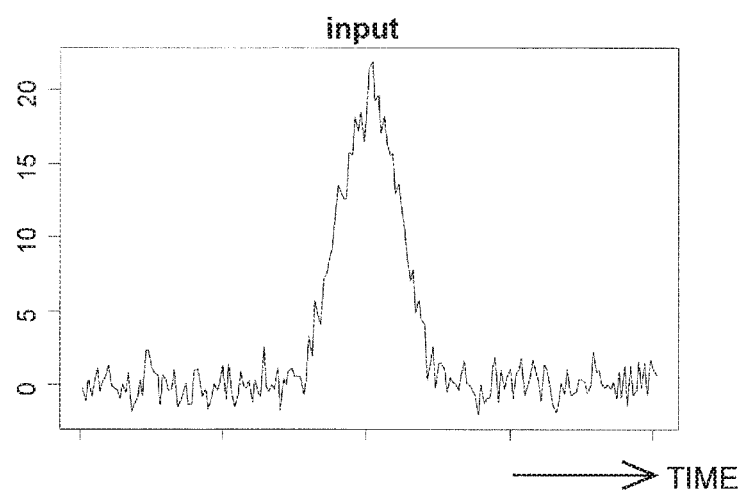
FIG. 4A illustrates original chromatogram data.
Figure 4B:
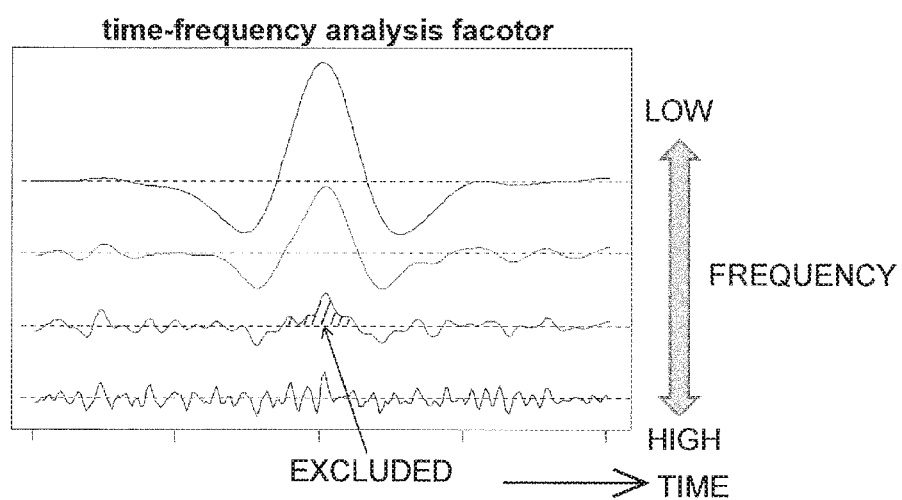
FIG. 4B illustrates waveform data obtained by a time-frequency analysis of the original data.

Initially, based on a determination of the analyzing frequencies by the user and a command to initiate the analysis, the time-frequency analyzer 18a performs a time-frequency analysis on the measurement data and obtains, for each of the frequencies specified by the user, a set of waveform data representing the temporal change in the intensity of the frequency component concerned in the chromatogram (Step S1). FIG. 4B shows waveform data obtained by performing a Mexican-hat continuous wavelet transform on a portion of the chromatogram (FIG. 4A). A Mexican-hat continuous wavelet transform is a technique in which a time-frequency analysis which is continuous in the frequency-axis direction is performed using a Mexican hat wavelet as the mother wavelet (localized wave), it is also possible to use a different type of mother wavelet (e.g. complex Morlet wavelet or Haar wavelet), or to employ a discrete wavelet transform, i.e. a time-frequency analysis which is discrete in the frequency-axis direction. Another method is to provide a window which divides the chromatogram into sections in the time-axis direction, and use a filter bank (or similar device) which performs a Fourier transform for each window. However, it should be noted that using the continuous wavelet transform is preferable in that continuous data can be obtained in both of the frequency-axis and time-axis directions.

Figure 5:
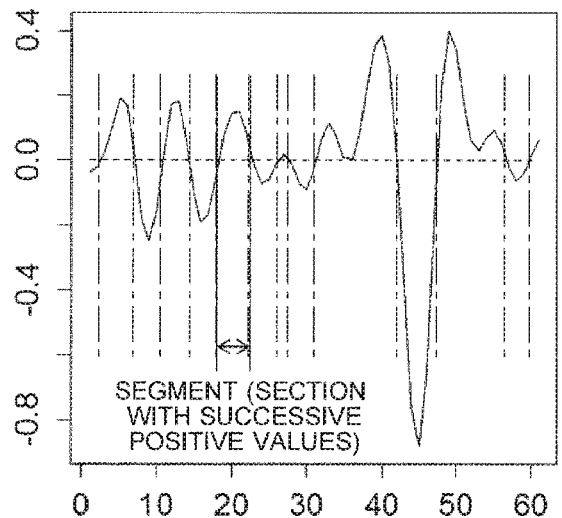
FIG. 5 is a diagram explaining the process of dividing waveform data into segments.

Subsequently, the segment divider 18b divides each of the plurality of sets of waveform data obtained at the plurality of frequencies by the time-frequency analysis into a plurality of segments so that each period of time Where positive values successively occur in the time-axis direction and each period of time where negative values successively occur are defined as one segment (Step S2). FIG. 5 shows one example of dividing one set of waveform data into segments.

Next, the segment value calculator 18c calculates the area of each of the segments of the waveform data obtained at the highest frequency. Then, it normalizes the area values based on the index data, stored in the storage section 16, to obtain segment values (Step S3). In other words, by using the temporal change in the noise factor recorded in the index data, the segment value calculator 18c calculates segment values which are free of the rise and fall of the noise level due to the noise factor. Subsequently, the selected segment group creator 18d calculates the average value and unbiased standard deviation σ of the segment values of the plurality of segments belonging to the same waveform data, and creates a selected segment group by excluding each segment whose segment value exceeds the average+Nσ (where N is a positive integer) from the segments constituting the waveform data concerned (FIG. 4B; Step S4).

In the previously described example, the area of each segment is normalized to obtain the segment value, and each segment whose segment value exceeds the average+Nσ is excluded. It is also possible to use the height in place of the area and/or to exclude each segment whose area or height exceeds the median+M×MAD (median absolute deviation, where M is a positive integer). As for N or M in the aforementioned formulae, a suitable value can be used for each set of measurement data taking into account the distribution of the segment values.

As noted earlier, if a peak is present in a chromatogram, area or height of a segment in the waveform increases as a result of the time-frequency analysis. Accordingly, by Step S4, peak components can be excluded from the waveform data.

Figure 6:
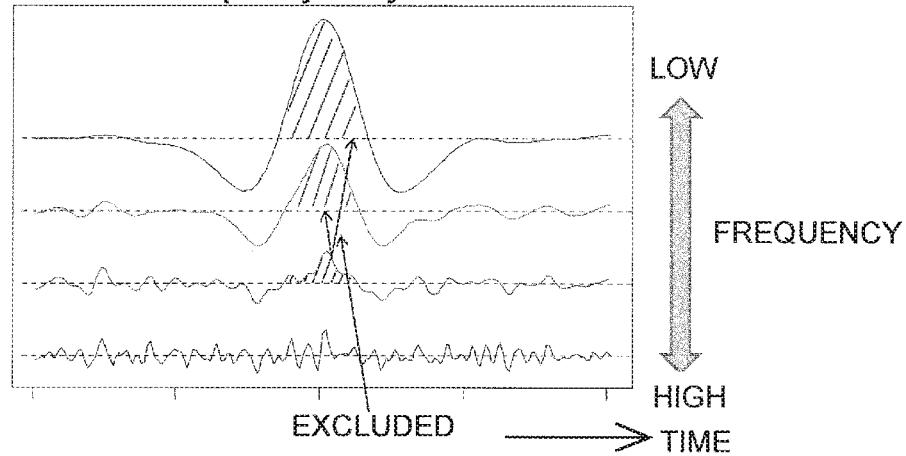
FIG. 6 is a diagram explaining the process of excluding segments at lower frequencies.

If there is any segment excluded by the selected segment group creator 18d (YES in Step S5), other segments located at the same position in the time-axis direction in the waveform data at the lower frequencies are also excluded (Step S6). If there is no segment excluded by the selected segment group creator 18d (NO in Step S5). The segment value calculator 18c once more calculates the segment value of each of the plurality of segments in the waveform data at the next highest frequency, i.e. the set of waveform data at the highest frequency among the sets of waveform data which remain unprocessed (Step S3). Then, a selected segment group is created in the previously described manner (Step S4), and if there is any segment excluded (YES in Step S5). Other segments located at the same position in the time-axis direction in the waveform data at the lower frequencies are excluded (Step S6; see FIG. 6).

As just described, if there is a peak component at a certain frequency, there is certainly a peak component within the frequency range lower than that frequency. Accordingly, by performing Step S6, a selected segment group from which peak components are more assuredly removed can be created.

As a result of sequentially creating the selected segment groups in descending order of the frequency, when the selected segment groups for all sets of waveform data have been created (YES Step S7), the noise level calculator 18e calculates the noise level from the average value of the areas of segments included in the selected segment groups for each frequency of the plurality of the frequencies (Step S8).

Figure 7:
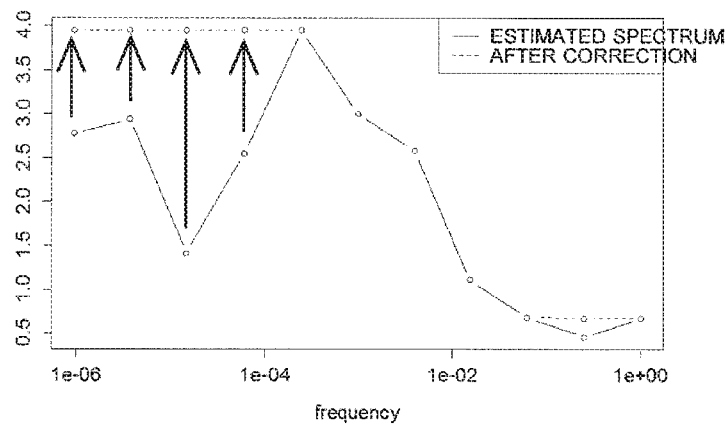
FIG. 7 is a diagram illustrating a noise-level correction.

As noted earlier, the capacitor or A/D converter included in a commonly used detector functions like a low-pass filter. Therefore, in a set of measurement data obtained through such a detector, signals within a high frequency range are relatively decreased. Accordingly, in order to reflect such a tendency, the noise level corrector 18f determines whether or not the noise level at lower frequencies is equal to or higher than the noise level at higher frequencies, and if not (NO in Step S9), the noise level corrector 18f corrects the calculated values of the noise level (Step S10) and determines the noise level at each frequency (Step S11). FIG. 7 shows one example of the noise-level correction.

It should be noted that Steps S5, S6, S9 and S10 are additional steps for calculating the noise level with high accuracy and are dispensable for the present invention. The normalization of the segment areas using the index data only needs to be performed when necessary; this process may be omitted in the case of a chromatogram obtained under fixed conditions (i.e. when it is possible to consider that there is no specific factor causing a temporal change in the noise level). That is to say, it is possible to independently create a selected segment group from the waveform data at each frequency, calculate the average or median of the segment values of the segments constituting the selected segment group, and directly adopt the calculated value as the noise level.

Although the previous embodiment is concerned with the case of processing a chromatogram obtained with a liquid chromatograph, the described method can also be used to determine the noise level in various other kinds of measurement data, such as an optical spectrum obtained through a spectrometric measurement or a mass spectrum obtained through mass spectrometry, other than a chromatogram acquired with a liquid chromatograph or gas chromatograph.

Additionally, as opposed to the previous embodiment in which waveform data are divided so that each period of time where positive values successively occur and each period of where negative values occur are defined as one segment, the waveform data may also be divided so that each period of time between a local maximum and a local minimum is defined as one segment.

REFERENCE SIGNS LIST

10 . . . Measurement Data Processing Device
11 . . . CPU
12 . . . Memory
14 . . . Input Unit
16 . . . Storage Section
17 . . . Communication Interface (I/F)
18 . . . Program for Processing Measurement Data.
   18a . . . Time-Frequency Analyzer
   18b . . . Segment Divider
   18c . . . Segment Value Calculator
   18d . . . Selected Segment Group Creator
   18e . . . Noise Level Calculator
   18f . . . Noise Level Corrector

The invention claimed is:

1. A noise level estimation method for estimating a magnitude of a noise component, the method comprising:
   a) obtaining measurement data including a peak component and the noise component, by measuring an intensity of a signal that changes with respect to a predetermined physical quantity, the measurement data being obtained through chromatography, spectrophotometry, or mass spectrometry;
   b) performing a time-frequency analysis on the measurement data to obtain, for each of a plurality of predetermined frequencies, waveform data representing a change in an intensity of a frequency component in the signal with respect to the predetermined physical quantity;
   c) dividing the waveform data of each of the plurality of predetermined frequencies into a plurality of segments so that each segment includes successive positive values or successive negative values in a direction of a change in the physical quantity, or so that each segment is between a local maximum and a local minimum neighboring each other in the direction of the change in the physical quantity;

d) determining a magnitude of each of the plurality of segments in the waveform data of each of the plurality of predetermined frequencies;

e) creating, for the waveform data of each of the plurality of predetermined frequencies, a selected segment group by excluding a segment whose magnitude exceeds a predetermined reference value from the plurality of segments in the waveform data; and f) determining a noise level of each of the plurality of predetermined frequencies by calculating an average or a median of the magnitudes of the segments included in the selected segment group.

2. The noise level estimation method according to claim 1, further comprising:

normalizing the magnitude of each of the plurality of segments before creating the selected segment group, using index data concerning a change in the magnitude of the noise component in the direction of the change in the physical quantity in the measurement data.

3. The noise level estimation method according to claim 2, wherein:

the selected segment group is created by excluding a segment which is located at a position corresponding to the aforementioned excluded segment in the direction of the change in the predetermined physical quantity and which belongs to the waveform data at a lower frequency than the frequency of the waveform data to which the aforementioned excluded segment belongs.

4. The noise level estimation method according to claim 3, further comprising:

comparing the noise levels at the plurality of predetermined frequencies with each other, and correcting the noise levels so that the noise level at a lower frequency becomes equal to or higher than the noise level at a higher frequency.

5. The noise level estimation method according to claim 2, further comprising:

comparing the noise levels at the plurality of predetermined frequencies with each other, and correcting the noise levels so that the noise level at a lower frequency becomes equal to or higher than the noise level at a higher frequency.

6. The noise level estimation method according to claim 1, wherein:

the selected segment group is created by excluding a segment which is located at a position corresponding to the aforementioned excluded segment in the direction of the change in the predetermined physical quantity and which belongs to the waveform data at a lower frequency than the frequency of the waveform data to which the aforementioned excluded segment belongs.

7. The noise level estimation method according to claim 6, further comprising:

comparing the noise levels at the plurality of predetermined frequencies with each other, and correcting the noise levels so that the noise level at a lower frequency becomes equal to or higher than the noise level at a higher frequency.

8. The noise level estimation method according to claim 1, further comprising:

comparing the noise levels at the plurality of predetermined frequencies with each other, and correcting the noise levels so that the noise level at a lower frequency becomes equal to or higher than the noise level at a higher frequency.

9. A measurement data processing device used for estimating a magnitude of a noise component, the device comprising:

a processor configured to:

a) obtain measurement data including a peak component and the noise component, by measuring an intensity of a signal that changes with respect to a predetermined physical quantity, the measurement data being obtained through chromatography, spectrophotometry, or mass spectrometry;

b) perform a time-frequency analysis on the measurement data to obtain, for each of a plurality of predetermined frequencies, waveform data representing a change in an intensity of a frequency component in the signal with respect to the predetermined physical quantity;

c) divide the waveform data of each of the plurality of predetermined frequencies into a plurality of segments so that each segment includes successive positive values or successive negative values in a direction of a change in the physical quantity, or so that each segment is between a local maximum and a local minimum neighboring each other in the direction of the change in the physical quantity;

d) determine a magnitude of each of the plurality of segments in the waveform data of each of the plurality of predetermined frequencies;

e) create, for the waveform data of each of the plurality of predetermined frequencies, a selected segment group by excluding a segment whose magnitude exceeds a predetermined reference value from the plurality of segments in the waveform data; and f) determine a noise level of each of the plurality of predetermined frequencies by calculating an average or a median of the magnitudes of the segments included in the selected segment group.

10. A non-transitory computer readable medium recording a program for estimating a magnitude of a noise component, the program causing a computer to:

a) obtain measurement data including a peak component and the noise component, by measuring an intensity of a signal that changes with respect to a predetermined physical quantity, the measurement data being obtained through chromatography, spectrophotometry, or mass spectrometry;

b) perform a time-frequency analysis on the measurement data to obtain, for each of a plurality of predetermined frequencies, waveform data representing a change in an intensity of a frequency component in the aforementioned signal with respect to the predetermined physical quantity;

c) divide the waveform data of each of the plurality of predetermined frequencies into a plurality of segments so that each segment includes successive positive values or successive negative values in a direction of a change in the physical quantity, or so that each segment is between a local maximum and a local minimum neighboring each other in the direction of the change in the physical quantity;

d) determine a magnitude of each of the plurality of segments in the waveform data of each of the plurality of predetermined frequencies;

e) create, for the waveform data of each of the plurality of predetermined frequencies, a selected segment group by excluding a segment whose magnitude exceeds a predetermined reference value from the plurality of segments in the waveform data; and f) determine a noise level of each of the plurality of predetermined frequencies by calculating an average or a median of the magnitudes of the segments included in the selected segment group.

\* \* \* \* \*